United States Patent
Gross (10) Patent No.: US 9,486,623 B2
(45) Date of Patent: Nov. 8, 2016

(54) ELECTRICAL STIMULATION OF A PANCREAS

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 14/639,613

(22) Filed: Mar. 5, 2015

(65) Prior Publication Data

US 2015/0251001 A1    Sep. 10, 2015

Related U.S. Application Data

(60) Provisional application No. 61/948,415, filed on Mar. 5, 2014.

(51) Int. Cl.
*A61N 1/00* (2006.01)
*A61N 1/05* (2006.01)
*A61N 1/36* (2006.01)

(52) U.S. Cl.
CPC .......... *A61N 1/056* (2013.01); *A61N 1/05* (2013.01); *A61N 1/36007* (2013.01)

(58) Field of Classification Search
USPC ............................................ 607/62
See application file for complete search history.

(56) References Cited

U.S. PATENT DOCUMENTS

| | | | |
|---|---|---|---|
| 5,368,028 A | 11/1994 | Palti | |
| 5,814,089 A | 9/1998 | Stokes et al. | |
| 5,919,216 A | 7/1999 | Houben et al. | |
| 6,135,978 A | 10/2000 | Houben et al. | |
| 7,228,178 B2 | 6/2007 | Carroll et al. | |
| 7,904,176 B2 | 3/2011 | Ben-Ezra et al. | |
| 7,991,467 B2 | 8/2011 | Markowitz et al. | |
| 8,019,421 B2 | 9/2011 | Darvish et al. | |
| 8,538,535 B2 | 9/2013 | Gross et al. | |
| 8,626,290 B2 | 1/2014 | Dagan et al. | |
| 8,626,299 B2 | 1/2014 | Gross et al. | |
| 8,649,863 B2 | 2/2014 | Gross et al. | |
| 8,855,783 B2 | 10/2014 | Dagan et al. | |
| 8,862,243 B2 | 10/2014 | Gross | |

(Continued)

FOREIGN PATENT DOCUMENTS

| | | |
|---|---|---|
| WO | WO0191854 | 12/2001 |
| WO | WO02053093 | 7/2002 |

(Continued)

OTHER PUBLICATIONS

An International Search Report and Written Opinion issued in PCT/IL2012/000336 on Mar. 5, 2013.

(Continued)

*Primary Examiner* — Nicole F Johnson
(74) *Attorney, Agent, or Firm* — Sughrue Mion, PLLC (57) ABSTRACT

Apparatus and methods are described, including a method that includes (i) identifying that it is desired to apply electrical stimulation to a pancreas of a subject, and (ii) in response to the identifying, placing an intravascular support structure within a blood vessel of the subject. The intravascular support structure has at least one electrode coupled thereto, the at least one electrode being configured to stimulate the pancreas of the subject by driving an electric current through tissue of the pancreas of the subject. Other applications are also described.

18 Claims, 5 Drawing Sheets

(56) References Cited

U.S. PATENT DOCUMENTS

| | | | |
|---|---|---|---|
| 9,005,106 | B2 | 4/2015 | Gross et al. |
| 2002/0026141 | A1 | 2/2002 | Houben et al. |
| 2002/0161414 | A1 | 10/2002 | Flesler et al. |
| 2003/0055464 | A1 | 3/2003 | Darvish et al. |
| 2004/0138722 | A1 | 7/2004 | Carroll et al. |
| 2004/0249421 | A1 | 12/2004 | Harel et al. |
| 2006/0074459 | A1 | 4/2006 | Flesler et al. |
| 2007/0016262 | A1 | 1/2007 | Gross et al. |
| 2007/0060812 | A1* | 3/2007 | Harel ............... A61B 5/04 600/347 |
| 2007/0092446 | A1 | 4/2007 | Haddad et al. |
| 2007/0156177 | A1 | 7/2007 | Harel et al. |
| 2007/0299320 | A1 | 12/2007 | Policker et al. |
| 2008/0033501 | A1 | 2/2008 | Gross |
| 2008/0065168 | A1 | 3/2008 | Bitton et al. |
| 2008/0215117 | A1 | 9/2008 | Gross |
| 2008/0275531 | A1* | 11/2008 | Bulkes ............ A61B 5/04282 607/62 |
| 2009/0030473 | A1 | 1/2009 | Khawaled et al. |
| 2009/0062881 | A1 | 3/2009 | Gross et al. |
| 2009/0131993 | A1 | 5/2009 | Rousso et al. |
| 2009/0171410 | A1 | 7/2009 | Benarie |
| 2009/0198308 | A1 | 8/2009 | Gross et al. |
| 2009/0281449 | A1 | 11/2009 | Thrower et al. |
| 2010/0298741 | A1 | 11/2010 | Gross et al. |
| 2010/0305392 | A1 | 12/2010 | Gross et al. |
| 2011/0118773 | A1 | 5/2011 | Gross et al. |
| 2011/0257561 | A1* | 10/2011 | Gertner ............ A61B 5/412 601/2 |
| 2011/0301670 | A1 | 12/2011 | Gross et al. |
| 2012/0035679 | A1 | 2/2012 | Dagan et al. |
| 2012/0083855 | A1 | 4/2012 | Gross et al. |
| 2013/0338748 | A1 | 12/2013 | Dagan |
| 2014/0114377 | A1 | 4/2014 | Dagan et al. |
| 2014/0180391 | A1 | 6/2014 | Dagan et al. |
| 2014/0324142 | A1 | 10/2014 | Dagan et al. |
| 2015/0005850 | A1 | 1/2015 | Gross |
| 2015/0151121 | A1 | 6/2015 | Dagan et al. |

FOREIGN PATENT DOCUMENTS

| | | |
|---|---|---|
| WO | WO02082968 | 10/2002 |
| WO | WO03045493 | 6/2003 |
| WO | WO 2004/021858 | 3/2004 |
| WO | WO 2004/112563 | 12/2004 |
| WO | WO 2004/112883 | 12/2004 |
| WO | WO 2005/007232 | 1/2005 |
| WO | WO 2005/087310 | 9/2005 |
| WO | WO 2006/018851 | 2/2006 |
| WO | WO 2006/087712 | 8/2006 |
| WO | WO 2006/102626 | 9/2006 |
| WO | WO 2006/129321 | 12/2006 |
| WO | WO 2007/080595 | 7/2007 |
| WO | WO 2008/117296 | 10/2008 |
| WO | WO 2008/139463 | 11/2008 |
| WO | WO2011092710 | 8/2011 |
| WO | WO2013035092 | 3/2013 |
| WO | WO2013164829 | 11/2013 |

OTHER PUBLICATIONS

An International Search Report and Written Opinion issued in PCT/IL2013/050375 on Aug. 8, 2013.

Bathien N et al., "Inhibition and synchronisation of tremor induced by a muscle twitch," Journal of Neurology, Neurosurgery, and Psychiatry, 1980, 43, 713-718.

Brereton H et al., "Islet alpha-cells do not influence insulin secretion from beta-cells through cell-cell contact," Feb. 2007;31(1):61-5 (abstract).

Jöbges EM et al., "Vibratory proprioceptive stimulation affects Parkinsonian tremor," Parkinsonism & Related Disorders, vol. 8, Issue 3, Jan. 2002, pp. 171-176 (abstract).

Kaszala K et al., "Device Sensing: Sensors and Algorithms for Pacemakers and Implantable Cardioverter Defibrillators," Circulation. 2010;122:1328-1340.

Matveyenko AV, "Pulsatile Portal Vein Insulin Delivery Enhances Hepatic Insulin Action and Signaling," Diabetes. Sep. 2012; 61(9): 2269-2279.

Mones RJ et al., "The response of the tremor of patients with Parkinsonism to peripheral nerve stimulation," J. Neurol. Neurosurg. Psychiat., 1969, 32, 512-518.

* cited by examiner

ELECTRICAL STIMULATION OF A PANCREAS

CROSS-REFERENCE TO RELATED APPLICATIONS

The present application claims the priority of U.S. Provisional Application 61/948,415 to Gross, entitled "Electrical Stimulation of a Pancreas," filed Mar. 5, 2014.

FIELD OF THE INVENTION

The present invention relates to apparatus and methods for stimulating a human pancreas.

BACKGROUND

Certain types of diabetes mellitus ("diabetes") are characterized by the failure of the pancreas to produce sufficient insulin.

SUMMARY OF THE INVENTION

Some applications of the present invention provide a method for treating a subject. First, it is identified that it is desired to apply electrical stimulation to the pancreas of the subject. In response to the identifying, an intravascular support structure (e.g., a stent) is placed within a blood vessel (e.g., the inferior vena cava) of the subject. The intravascular support structure has at least one electrode coupled thereto. The at least one electrode is configured to stimulate the pancreas of the subject by driving an electric current through tissue of the pancreas.

Alternatively or additionally, it is identified that the subject is eating. In response to the identifying, a plurality of electrodes disposed within the subject's body is driven to stimulate the pancreas of the subject by driving an electric current through tissue of the pancreas. The stimulating occurs during a first period of time, which begins less than 15 minutes after the identifying and has a duration of at least 10 minutes. Then, during a second period of time that immediately follows the first period of time and has a duration of at least 30 minutes, the plurality of electrodes is not driven to stimulate the pancreas of the subject.

There is therefore provided, in accordance with some applications of the present invention, a method including:
identifying that it is desired to apply electrical stimulation to a pancreas of a subject; and
in response to the identifying, placing an intravascular support structure within a blood vessel of the subject, the intravascular support structure having at least one electrode coupled thereto, the at least one electrode being configured to stimulate the pancreas of the subject by driving an electric current through tissue of the pancreas of the subject.

In some applications, placing the intravascular support structure within the blood vessel of the subject includes placing the intravascular support structure within an inferior vena cava of the subject.

In some applications, placing the intravascular support structure within the inferior vena cava includes penetrating a wall of the inferior vena cava with the at least one electrode that is coupled to the intravascular support structure.

In some applications, penetrating the wall of the inferior vena cava includes penetrating completely through the wall of the inferior vena cava.

In some applications, placing the intravascular support structure within the inferior vena cava includes placing the intravascular support structure between the superior mesenteric vein and the portal vein.

In some applications,
at least a portion of an element selected from the group consisting of: the intravascular support structure, and the at least one electrode, is radiopaque,
the method further includes viewing a fluoroscopic image of the radiopaque portion, when the radiopaque portion is inside the inferior vena cava, and
placing the intravascular support structure within the inferior vena cava of the subject includes aligning the at least one electrode with respect to the pancreas, in response to the viewing.

In some applications, placing the intravascular support structure within the inferior vena cava of the subject includes:
using a catheter to deliver the intravascular support structure to a site within the inferior vena cava;
placing the intravascular support structure at the site; and
following the placing, aligning the at least one electrode with respect to the pancreas in response to viewing a rotation indicator on a handle of the catheter.

In some applications, the at least one electrode includes at least two electrodes, and placing the intravascular support structure within the inferior vena cava of the subject includes placing the intravascular support structure to which are coupled the at least two electrodes within the inferior vena cava of the subject.

In some applications, the method further includes using a control unit to drive the at least one electrode to drive the electric current by sending a signal to the electrode.

In some applications, using the control unit to drive the at least one electrode to drive the electric current includes using the control unit to drive the at least one electrode from outside a body of the subject.

In some applications, the method further includes identifying that the subject is eating, and using the control unit to drive the at least one electrode to drive the electric current includes:
in response to the identifying, during a first period of time beginning less than 15 minutes after the identifying and having a duration of at least 10 minutes, driving the at least one electrode to drive the electric current; and
during a second period of time that immediately follows the first period of time and has a duration of at least 30 minutes, withholding driving the at least one electrode to drive the electric current.

In some applications, driving the at least one electrode to drive the electric current during the first period of time includes driving the at least one electrode to drive the electric current during a period of time that begins less than 10 minutes after the identifying.

In some applications, driving the at least one electrode to drive the electric current during the period of time that begins less than 10 minutes after the identifying includes driving the at least one electrode to drive the electric current during a period of time that begins less than 5 minutes after the identifying.

In some applications, driving the at least one electrode to drive the electric current during the first period of time includes driving the at least one electrode to drive the electric current during a period of time having a duration of less than 30 minutes.

In some applications, driving the at least one electrode to drive the electric current during the period of time having a duration of less than 30 minutes includes driving the at least one electrode to drive the electric current during a period of time having a duration of less than 20 minutes.

In some applications, withholding driving the at least one electrode to drive the electric current during the second period of time includes withholding driving the at least one electrode to drive the electric current during a period of time having a duration of at least 50 minutes.

In some applications, withholding driving the at least one electrode to drive the electric current during the second period of time includes withholding driving the at least one electrode to drive the electric current during a period of time having a duration of less than 90 minutes.

In some applications, using the control unit to drive the at least one electrode to drive the electric current includes using the control unit to drive the at least one electrode to drive a current having a frequency between 2 and 20 Hz.

In some applications, using the control unit to drive the at least one electrode to drive the electric current includes using the control unit to drive the at least one electrode to drive a current having an amplitude between 1 and 8 mA.

In some applications,
the at least one electrode includes at least a first electrode, a second electrode, and a third electrode, and
using the control unit to drive the at least one electrode to drive the electric current includes using the control unit to:
drive the first electrode and the second electrode to drive a first electric current therebetween,
drive the first electrode and the third electrode to drive a second electric current therebetween, and
drive the second electrode and the third electrode to drive a third electric current therebetween.

In some applications, the method further includes using a sensor to detect that the subject is eating, and using the control unit to drive the at least one electrode to drive the electric current includes using the control unit to drive the at least one electrode to drive the electric current in response to detecting that the subject is eating.

In some applications, using the control unit to drive the at least one electrode includes withholding driving the at least one electrode at one or more designated times in a 24-hour cycle.

In some applications, the method further includes using a sensor to detect a physiological parameter of the subject, and using the control unit to drive the at least one electrode to drive the electric current includes using the control unit to drive the at least one electrode to drive the electric current in response to the detected physiological parameter.

In some applications, using the sensor to detect the physiological parameter of the subject includes using the sensor to detect a blood-glucose level of the subject, and using the control unit to drive the at least one electrode to drive the electric current includes using the control unit to drive the at least one electrode to drive the electric current in response to the blood-glucose level of the subject.

In some applications, using the sensor to detect the physiological parameter of the subject includes using the sensor to detect a blood-insulin level of the subject, and using the control unit to drive the at least one electrode to drive the electric current includes using the control unit to drive the at least one electrode to drive the electric current in response to the blood-insulin level of the subject.

In some applications, using the sensor to detect the physiological parameter of the subject includes using the sensor to detect a heart rate of the subject, and using the control unit to drive the at least one electrode to drive the electric current includes using the control unit to drive the at least one electrode to drive the electric current in response to the heart rate of the subject.

In some applications, using the control unit to drive the at least one electrode to drive the electric current includes using the control unit to drive the at least one electrode to drive a sequence of bursts of electric current, the bursts being separated by respective time intervals, each of which having a duration of between 2 and 8 minutes.

In some applications, using the control unit to drive the at least one electrode to drive the electric current includes using the control unit to drive the at least one electrode to drive the electric current in response to a time of day.

In some applications, the method further includes:
implanting a receiving antenna in the subject, the receiving antenna being configured to receive the signal from the control unit;
passing a wire through a wall of the blood vessel; and
by connecting the antenna to the electrode via the wire, facilitating the driving of the electrode by the control unit.

In some applications, the method further includes implanting a control unit in the subject, the control unit being configured to drive the at least one electrode to drive the electric current.

In some applications, the method further includes:
providing a power source;
passing a wire through a wall of the blood vessel; and
by connecting the power source to the electrode via the wire, facilitating powering of the electrode by the power source.

In some applications, the method further includes implanting a power source in the subject, the power source being configured to power the electrode.

In some applications, placing the intravascular support structure within the blood vessel of the subject includes placing the intravascular support structure within an aorta of the subject.

There is further provided, in accordance with some applications of the present invention, a method including:
identifying that it is desired to apply electrical stimulation to a pancreas of a subject; and
in response to the identifying:
implanting a control unit in the subject,
placing a distal end of at least one lead within a blood vessel of the subject, within 2 cm of the pancreas of the subject, and
connecting a proximal end of the lead to the control unit.

There is further provided, in accordance with some applications of the present invention, apparatus for stimulating a pancreas of a subject, the apparatus including:
an intravascular support structure configured to be placed within a blood vessel of the subject;
at least one electrode coupled to the intravascular support structure, the at least one electrode being configured to stimulate the pancreas of the subject by driving an electric current through tissue of the pancreas; and
a control unit configured to drive the at least one electrode to drive the electric current by sending a signal to the electrode.

In some applications, the at least one electrode includes a plurality of electrodes.

In some applications, a distance between a proximalmost one of the plurality of electrodes and a distalmost one of the plurality of electrodes is between 2 and 7 cm.

In some applications, the apparatus further includes an eating sensor configured to detect that the subject is eating, and the control unit is configured to drive the at least one electrode to drive the electric current in response to the eating sensor detecting that the subject is eating.

In some applications, the apparatus further includes a physiological sensor configured to detect a physiological parameter of the subject, and the control unit is configured to drive the at least one electrode to drive the electric current in response to the physiological parameter.

In some applications, the physiological sensor includes a blood-glucose sensor configured to detect a blood-glucose level of the subject, and the control unit is configured to drive the at least one electrode to drive the electric current in response to the detected blood-glucose level of the subject.

In some applications, the physiological sensor includes a blood-insulin sensor configured to detect a blood-insulin level of the subject, and the control unit is configured to drive the at least one electrode to drive the electric current in response to the detected blood-insulin level of the subject.

In some applications, the physiological sensor includes a heart-rate sensor configured to detect a heart rate of the subject, and the control unit is configured to drive the at least one electrode to drive the electric current in response to the detected heart rate of the subject.

In some applications, the apparatus further includes a power source configured to supply power to the at least one electrode.

In some applications, the power source is wiredly connected to the electrode.

In some applications, the power source is coupled to the support structure.

In some applications, the power source is configured to wirelessly supply power to the at least one electrode.

In some applications, the control unit is further configured to wirelessly supply power to the at least one electrode.

In some applications, the apparatus further includes a wireless transmission device, and the control unit is configured to drive the wireless transmission device to send the signal to the electrode.

In some applications, the apparatus further includes at least one lead connected to the control unit, the electrode being a distal end of the lead.

In some applications, the intravascular support structure includes:
a longitudinal element having a proximal end and a distal end;
a first stabilizing ring coupled to the proximal end of the longitudinal element; and
a second stabilizing ring coupled to the distal end of the longitudinal element,
both the first stabilizing ring and the second stabilizing ring being configured to stabilize the intravascular support structure by contacting a wall of the blood vessel.

In some applications, the at least one electrode is coupled to the longitudinal element.

In some applications, the at least one electrode is coupled to a ring selected from the group consisting of: the first stabilizing ring, and the second stabilizing ring.

In some applications, a length of the longitudinal element is between 3 and 10 cm.

In some applications,
the at least one electrode has a cross-section that has a perimeter consisting of first and second contiguous portions thereof,
along the first contiguous portion of the perimeter, the electrode is insulated, and
along the second contiguous portion of the perimeter, the electrode is not insulated,
the first contiguous portion including at least 50% of the perimeter.

In some applications, the first contiguous portion includes at least 65% of the perimeter.

In some applications, the control unit is coupled to the support structure.

In some applications, the apparatus further includes:
a receiving antenna configured to receive the signal from the control unit; and
a wire connecting the antenna to the electrode.

In some applications, the antenna is coupled to the support structure.

There is further provided, in accordance with some applications of the present invention, a method of stimulating a pancreas of a subject, the method including:
identifying that the subject is eating;
in response to the identifying, during a first period of time beginning less than 15 minutes after the identifying and having a duration of at least 10 minutes, driving a plurality of electrodes disposed within a body of the subject to stimulate the pancreas of the subject by driving an electric current through tissue of the pancreas of the subject; and
during a second period of time that immediately follows the first period of time and has a duration of at least 30 minutes, withholding driving the plurality of electrodes to stimulate the pancreas of the subject.

In some applications, driving the at least one electrode to drive the electric current during the first period of time includes driving the at least one electrode to drive the electric current during a period of time that begins less than 10 minutes after the identifying.

In some applications, driving the at least one electrode to drive the electric current during the period of time that begins less than 10 minutes after the identifying includes driving the at least one electrode to drive the electric current during a period of time that begins less than 5 minutes after the identifying.

In some applications, driving the at least one electrode to drive the electric current during the first period of time includes driving the at least one electrode to drive the electric current during a period of time having a duration of less than 30 minutes.

In some applications, driving the at least one electrode to drive the electric current during the period of time having a duration of less than 30 minutes includes driving the at least one electrode to drive the electric current during a period of time having a duration of less than 20 minutes.

In some applications, withholding driving the at least one electrode to drive the electric current during the second period of time includes withholding driving the at least one electrode to drive the electric current during a period of time having a duration of at least 50 minutes.

In some applications, withholding driving the at least one electrode to drive the electric current during the second period of time includes withholding driving the at least one electrode to drive the electric current during a period of time having a duration of less than 90 minutes.

In some applications, the method further includes, before identifying that the subject is eating, driving the plurality of electrodes to stimulate the pancreas of the subject with a basal level of stimulation that is less than a level of the stimulation that is in response to the identifying.

In some applications, driving the plurality of electrodes to stimulate the pancreas of the subject with the basal level of stimulation includes driving the plurality of electrodes to continuously stimulate the pancreas of the subject with the basal level of stimulation.

In some applications, driving the plurality of electrodes to stimulate the pancreas of the subject with the basal level of stimulation includes driving the plurality of electrodes to periodically stimulate the pancreas of the subject with the basal level of stimulation.

There is further provided, in accordance with some applications of the present invention, a method of stimulating a pancreas of a subject, the method including:

administering an agent selected from the group consisting of: a glucagon-secretion-inhibiting agent, and a glucagon antagonist, to the subject; and while the subject is affected by the administered agent, driving at least one electrode disposed within a blood vessel of the subject to stimulate the pancreas of the subject by driving an electric current through tissue of the pancreas of the subject.

There is further provided, in accordance with some applications of the present invention, a method for use with a blood-glucose-reduction device, the method including:

using a sensor, sensing a parameter indicative of a level of skeletomotor activity of a subject, and generating a signal in response thereto; and in response to the signal from the sensor indicating that the level of skeletomotor activity exceeds a skeletomotor-activity threshold, reducing reduction of blood glucose of the subject by the blood-glucose-reduction device.

In some applications, the sensor includes an accelerometer coupled to the subject, the method including reducing reduction of blood glucose of the subject by the blood-glucose-reduction device in response to a signal from the accelerometer indicating that the level of skeletomotor activity exceeds the skeletomotor-activity threshold.

In some applications, the accelerometer is implanted in the subject, the method including reducing reduction of blood glucose of the subject by the blood-glucose-reduction device in response to the signal from the accelerometer indicating that the level of skeletomotor activity exceeds the skeletomotor-activity threshold.

In some applications, reducing reduction of blood glucose of the subject by the blood-glucose-reduction device includes reducing reduction of blood glucose of the subject by the blood-glucose-reduction device in response to the signal from the sensor indicating that the subject is running.

In some applications, the sensor includes a heart-rate sensor, the method including reducing reduction of blood glucose of the subject by the blood-glucose-reduction device in response to a signal from the heart-rate sensor indicating that a heart rate of the subject exceeds a heart-rate threshold.

In some applications, the sensor includes a breathing-rate sensor, the method including reducing reduction of blood glucose of the subject by the blood-glucose-reduction device in response to a signal from the breathing-rate sensor indicating that a breathing rate of the subject exceeds a breathing-rate threshold.

In some applications, the blood-glucose-reduction device is a pancreatic stimulator, the method being for use with the pancreatic stimulator.

In some applications, the blood-glucose-reduction device is an insulin pump, the method being for use with the insulin pump.

There is further provided, in accordance with some applications of the present invention, a method for use with a blood-glucose-reduction device, the method including:

using a sensor, sensing a parameter indicative of a level of skeletomotor activity of a subject, and generating a signal in response thereto; and in response to the signal from the sensor indicating that the subject is likely to be sleeping, reducing reduction of blood glucose of the subject by the blood-glucose-reduction device.

In some applications, the sensor includes an accelerometer coupled to the subject, the method including reducing reduction of blood glucose of the subject by the blood-glucose-reduction device in response to a signal from the accelerometer indicating that the subject is lying down.

In some applications, the sensor includes a heart-rate sensor, the method including reducing reduction of blood glucose of the subject by the blood-glucose-reduction device in response to a signal from the heart-rate sensor indicating that a heart rate of the subject is less than a heart-rate threshold.

In some applications, the sensor includes a breathing-rate sensor, the method including reducing reduction of blood glucose of the subject by the blood-glucose-reduction device in response to a signal from the breathing-rate sensor indicating that a breathing rate of the subject is less than a breathing-rate threshold.

There is further provided, in accordance with some applications of the present invention, apparatus including:

a sensor, configured to sense a parameter indicative of a level of skeletomotor activity of a subject, and to generate a signal in response thereto; and a blood-glucose-reduction device, configured to modulate a reduction of blood glucose of the subject in response to the signal from the sensor.

In some applications, the blood-glucose-reduction device is a pancreatic stimulator.

In some applications, the blood-glucose-reduction device is an insulin pump.

The present invention will be more fully understood from the following detailed description of applications thereof, taken together with the drawings, in which:

DETAILED DESCRIPTION OF APPLICATIONS

Figure 1:
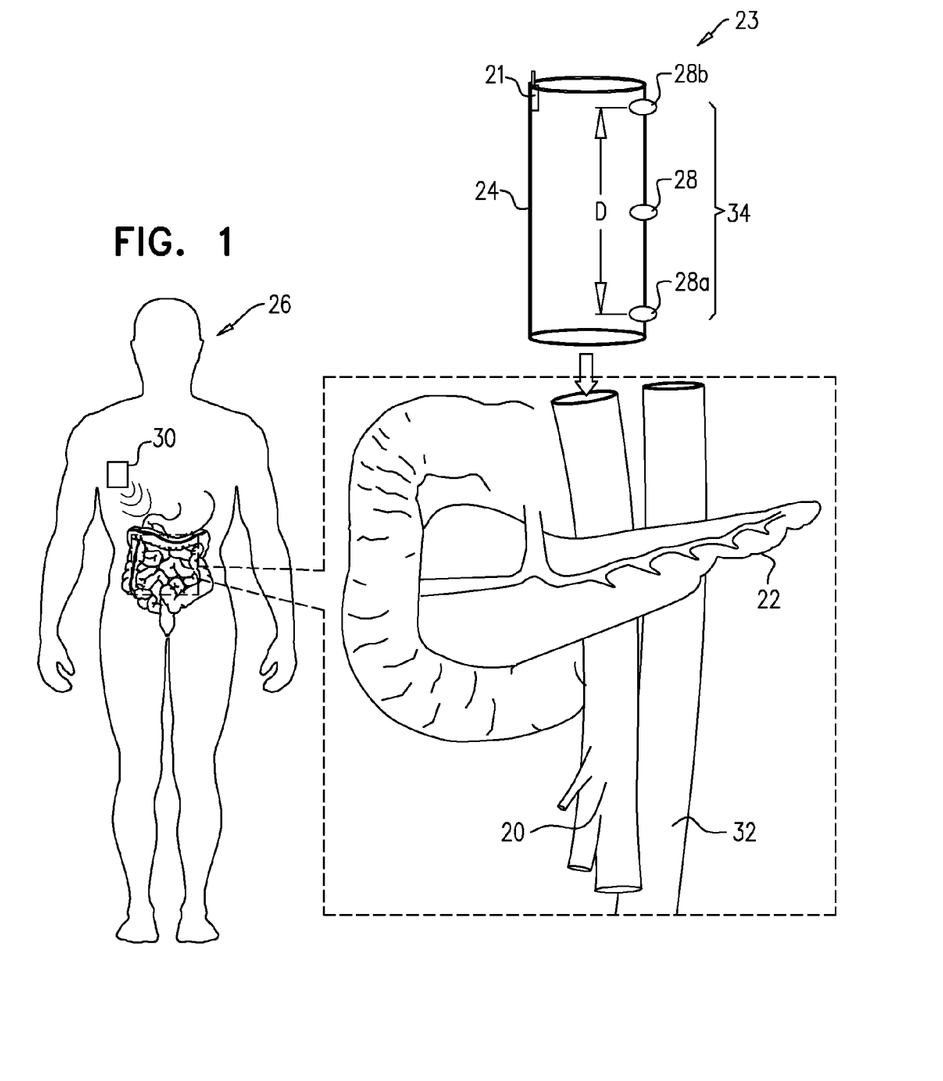
FIGS. 1-2 are schematic illustrations of apparatus for stimulating a pancreas of a subject, in accordance with some applications of the present invention.

Reference is made to FIG. 1, which is a schematic illustration of apparatus 23 for stimulating a pancreas 22 of a subject 26, in accordance with some applications of the present invention. FIG. 1 also includes a drawing of pancreas 22 and anatomy in the vicinity of the pancreas.

Apparatus 23 comprises an intravascular support structure 24 (e.g., a stent) configured to be placed within a blood vessel of subject 26. At least one electrode 28 is coupled to intravascular support structure 24, electrodes 28 being configured to stimulate pancreas 22 by driving an electric current through tissue of the pancreas. For convenience, the present description refers to "electrodes" in the plural. The stimulation provided by the electrodes may be monopolar or bipolar.

Intravascular support structure 24 is placed in the blood vessel of subject 26 in response to identifying that it is desired to apply electrical stimulation to pancreas 22 of the subject. For example, intravascular support structure 24 may be placed in the blood vessel in response to identifying that subject 26 is diabetic, and that the subject's pancreas does not produce enough insulin.

Apparatus 23 also comprises a control unit 30 configured to drive electrodes 28 to drive the electric current by sending a signal to the electrodes. Although control unit 30 is typically implanted in subject 26, in some applications, the control unit drives the electrodes from outside the subject's body. Typically, a receiving antenna 21 is implanted in the subject, to facilitate receiving the signal from the control unit. For example, as shown in FIG. 1, antenna 21 may be disposed on intravascular support structure 24, such that the intravascular support structure is wirelessly connected to control unit 30 via antenna 21. (A wireless transmission device, which sends the signal to the antenna, is shown in the figures as being an integrated part of the control unit.) Alternatively, as described immediately hereinbelow with reference to scenario A of FIG. 7, the antenna may be implanted remotely from the intravascular support structure.

Figure 7:
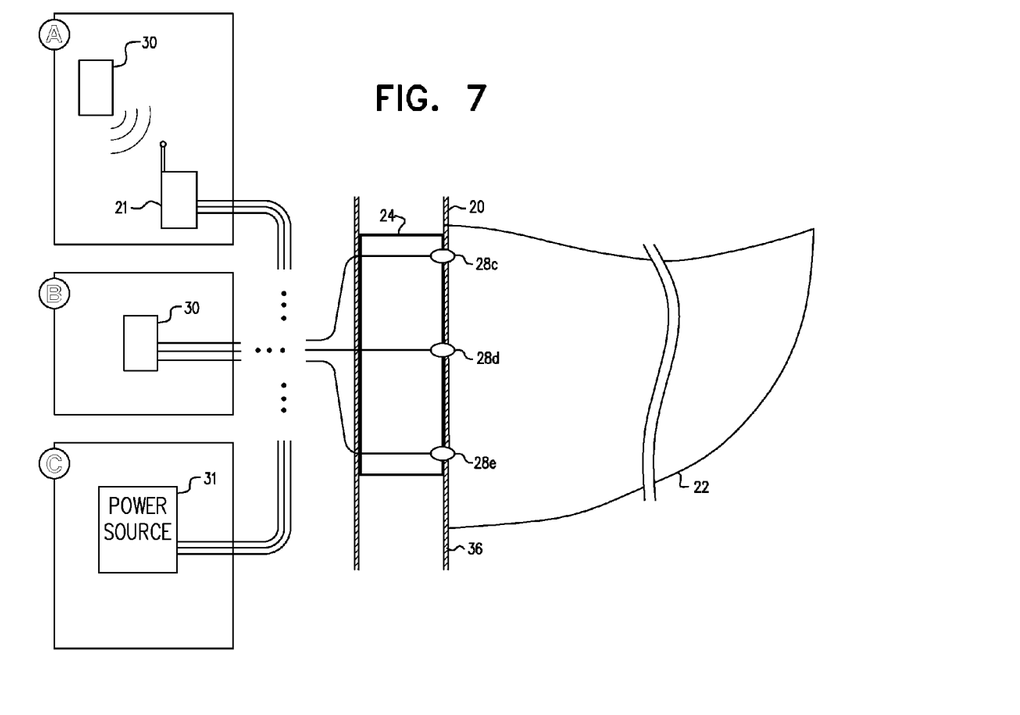
FIG. 7 is a schematic illustration of apparatus for stimulating a pancreas of a subject, in accordance with some applications of the present invention.

Reference is now additionally made to FIG. 7, which is a schematic illustration of apparatus 23, in accordance with some applications of the present invention. (Although the electrodes are shown penetrating the wall of the blood vessel, it is noted that the electrodes need not necessarily penetrate the wall, as described hereinbelow with reference to FIG. 2.) In some applications, one or more wires or leads 29 are passed through the wall of the blood vessel, and are used to connect a device that is outside the blood vessel to the electrodes, thus facilitating the control and/or powering of the electrodes. For example:

(i) As shown in scenario A, the electrodes may be connected to antenna 21 via the wired connection.

(ii) As shown in scenario B, the electrodes may be directly connected to control unit 30 via the wired connection, i.e., intravascular support structure 24 may be directly connected to control unit 30 via the lead that passes through the wall of the blood vessel.

(iii) As shown in scenario C, the electrodes may be connected to a power source 31 via the wired connection. Typically, the power source is implanted in the subject.

It is noted that the scope of the present invention includes wiredly connecting the electrodes to more than one device. For example, the electrodes may be connected both to (a) the antenna or control unit, and (b) power source 31. The scope of the present invention also includes coupling the power source and/or the control unit to the support structure.

In some applications, control unit 30 wirelessly supplies power to electrodes 28 via antenna 21. (In other words, power source 31 is configured to wirelessly supply power to the electrodes, and the control unit drives the power source to wirelessly supply the power.) In such applications, the control unit typically drives the electrodes to stimulate the pancreas by supplying the power. In other words, the control unit determines when the pancreas should be stimulated (as described hereinbelow, for example, with reference to FIG. 2), and supplies power to the electrodes at the appropriate times. In other applications, the electrodes are wiredly or wirelessly connected to a power source that constantly supplies power (e.g., as shown in scenario C of FIG. 7), but do not stimulate the pancreas until the control unit sends an appropriate signal.

Typically, control unit 30 drives electrodes 28 to drive a current having a frequency that is at least 2 Hz, less than 20 Hz, and/or between 2 and 20 Hz. Alternatively or additionally, the amplitude of the current is at least 1 mA, less than 8 mA, and/or between 1 and 8 mA.

Typically, as shown in FIG. 1, a plurality 34 of electrodes 28 (i.e., at least two electrodes 28) are coupled to intravascular support structure 24. In such applications, respective pairs of electrodes 28 may be driven to drive electric current between one another, e.g., as described hereinbelow with reference to FIG. 2. In other applications, a single electrode 28 is coupled to intravascular support structure 24, and electric current is driven between electrode 28 and another electrode that may be disposed outside of the blood vessel. For applications in which a plurality 34 of electrodes is coupled to intravascular support structure 24, a distance D between a proximalmost electrode 28a of plurality 34 and a distalmost electrode 28b of plurality 34 is between 2 and 7 cm. (In the present context, proximalmost electrode 28a is the electrode that is closest to the orifice through which the implant is placed in subject 26, e.g., a femoral vein incision.) Distance D generally corresponds to a typical width of a pancreas. (As shown in FIG. 2, in the context of the present description, the width "W" of the pancreas is generally measured along the longitudinal axis of the blood vessel in which intravascular support structure 24 is placed.)

Typically, intravascular support structure 24 is placed within inferior vena cava 20, typically between the superior mesenteric vein and the portal vein, as shown in FIG. 1. In some applications, intravascular support structure 24 is placed within the aorta 32 of the subject. Typically, the blood vessel in which intravascular support structure 24 is placed, and the transvascular access thereto, are relatively straight, such that the intravascular support structure is not required to have joints that facilitate bending.

Figure 2:
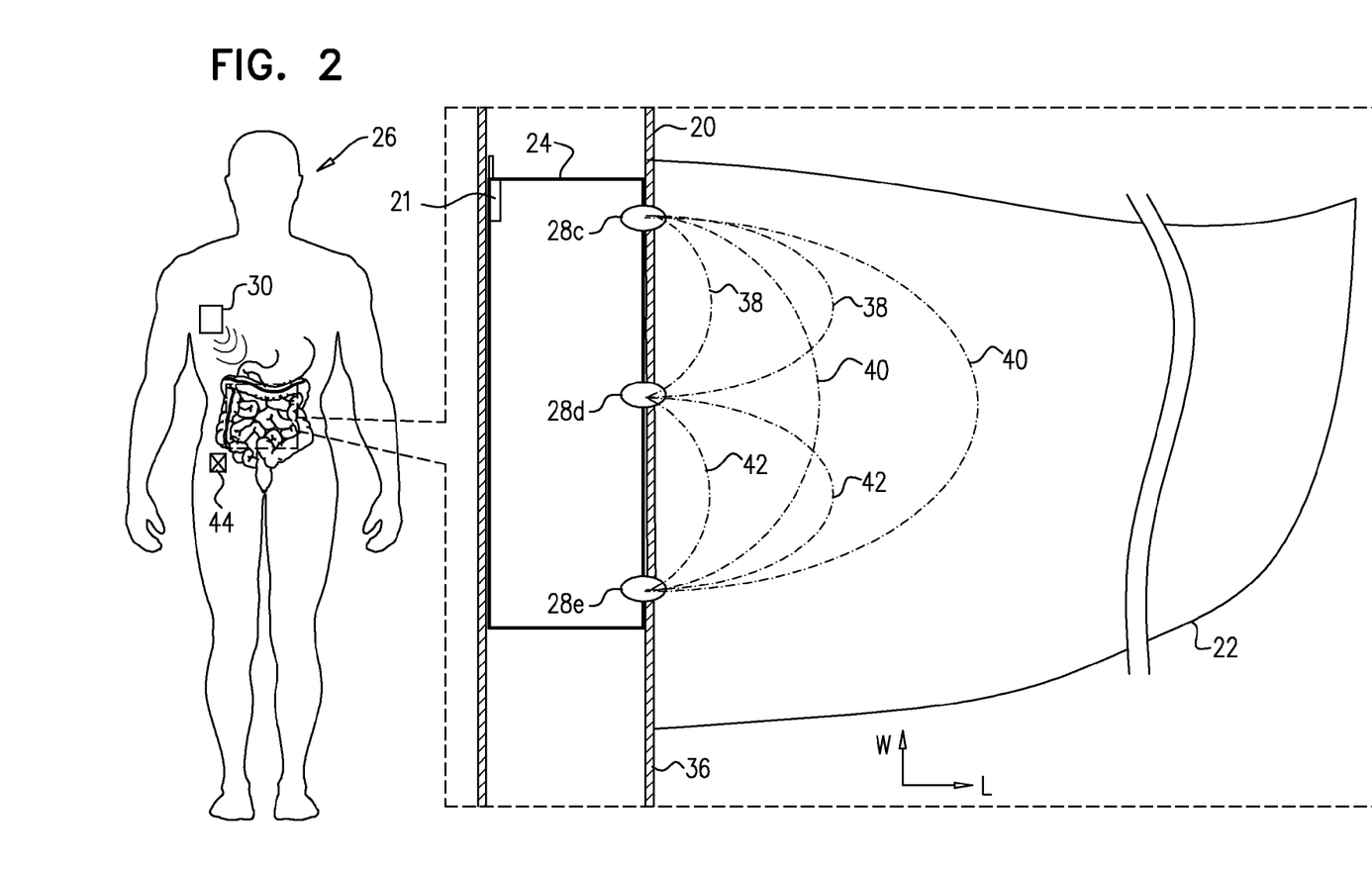

Reference is now made to FIG. 2, which is a schematic illustration of apparatus for stimulating pancreas 22 of subject 26, in accordance with some applications of the present invention. In some applications, as shown in FIG. 2, placing intravascular support structure 24 within inferior vena cava 20 comprises penetrating a wall 36 of inferior vena cava 20 with electrodes 28. In some applications, wall 36 is partially penetrated, while in other applications, wall 36 is completely penetrated, such that electrodes are disposed completely outside of inferior vena cava 20 (typically not penetrating the pancreas). In other applications, the electrodes do not at all penetrate the wall of the blood vessel inside of which they are disposed.

In some applications, at least a portion of intravascular support structure 24 and/or electrodes 28 is radiopaque, and intravascular support structure 24 is placed within inferior vena cava 20 in response to viewing a fluoroscopic image of the radiopaque portion, when the radiopaque portion is inside inferior vena cava 20. Viewing the fluoroscopic image facilitates the alignment of electrodes 28 with respect to the pancreas. For example, in response to viewing the fluoroscopic image, the physician may rotate intravascular support structure 24 about its longitudinal axis, such that electrodes 28 are made to face the pancreas. In some applications, the alignment of electrodes 28 is facilitated by a rotation indicator on the handle of a catheter that is used to deliver intravascular support structure 24. For example, following the placement of intravascular support structure 24 at the placement site in the inferior vena cava, the physician may rotate the catheter until the rotation indicator is aligned with a predetermined marker. The alignment of the rotation indicator with the marker indicates that electrodes 28 are facing the pancreas.

In some applications, as shown in FIG. 2, plurality 34 includes at least a first electrode 28*c*, a second electrode 28*d*, and a third electrode 28*e*. Control unit 30 drives (i) first electrode 28*c* and second electrode 28*d* to drive a first electric current 38 therebetween, (ii) first electrode 28*c* and third electrode 28*e* to drive a second electric current 40 therebetween, and (iii) second electrode 28*d* and third electrode 28*e* to drive a third electric current 42 therebetween. In this manner, pancreas 22 may be stimulated at a plurality of locations along its length L and width W. In particular, as shown in FIG. 2, stimulating pancreatic tissue that is relatively far from the electrodes (along the "L" axis) may be facilitated by driving an electric current between two electrodes that are relatively far from one another; conversely, stimulating pancreatic tissue that is relatively close to the electrodes may be facilitated by driving an electric current between two electrodes that are relatively close to one another. Alternatively or additionally, the "reach" of the stimulation may be adjusted by adjusting the power of the stimulating current.

FIG. 2 also shows a sensor 44 implanted in, or otherwise coupled to, subject 26. In some applications, sensor 44 comprises a physiological sensor configured to detect a physiological parameter of the subject. Sensor 44 may comprise, for example, an eating sensor, a blood-glucose sensor, a heart-rate sensor, a breathing-rate sensor, and/or a blood-insulin sensor. Alternatively or additionally, sensor 44 may comprise an accelerometer, configured to detect a level of skeletomotor activity of the subject.

In some applications, control unit 30 is configured to drive electrodes 28 to stimulate the pancreas in response to the detected physiological parameter, which is received via a signal from sensor 44. For example, control unit 30 may drive electrodes 28 in response to an eating sensor detecting that subject 26 is eating, and/or in response to a blood-glucose sensor detecting that the blood-glucose level of subject 26 is higher than desired, and/or in response to a blood-insulin sensor detecting that the blood-insulin level of subject 26 is lower than desired.

Alternatively or additionally, the control unit may at times reduce the reduction of glucose by the electrodes, in response to the signal from sensor 44 indicating that the level of the subject's skeletomotor activity exceeds a skeletomotor-activity threshold. For example, in response to a heart-rate sensor indicating the heart rate of the subject exceeds a heart-rate threshold, or a breathing-rate sensor indicating that the breathing rate of the subject exceeds a breathing-rate threshold, the control unit may inhibit the electrodes from stimulating the pancreas. Since a relatively high heart rate or breathing rate may be indicative of a relatively high level of skeletomotor activity (e.g., running), the control unit inhibits stimulation of the pancreas, in order to help keep the subject's level of blood glucose sufficiently high for maintaining the skeletomotor activity. Similarly, if an accelerometer detects that the level of skeletomotor activity exceeds the skeletomotor-activity threshold, the control unit may inhibit the electrodes from stimulating the pancreas.

It has been observed that blood-glucose levels tend to naturally decrease during sleep, and that hypoglycemia occurs in some sleeping diabetic patients. Accordingly, in some applications, the reduction of blood glucose by apparatus 23 is reduced in response to the signal from sensor 44 indicating that the subject is likely to be sleeping. For example, the control unit may inhibit the electrodes from stimulating the pancreas in response to (i) an accelerometer indicating that the subject is lying down (e.g., for a period of time that exceeds some predefined threshold), (ii) a heart-rate sensor indicating that the heart rate of the subject is less than a heart-rate threshold, or (iii) a breathing-rate sensor indicating that the breathing rate of the subject is less than a breathing-rate threshold.

In general, the techniques described above with reference to sensor 44 may be applied to any type of blood-glucose-reduction device, i.e., the blood-glucose-reduction device may be configured to modulate its reduction of blood glucose of the subject in response to the signal from the sensor. Examples of blood-glucose-reduction devices include pancreatic stimulators (such as any of the applications described herein) and insulin pumps.

Alternatively or additionally, control unit 30 may be configured to drive electrodes 28 in response to a time of day. For example, control unit 30 may drive electrodes 28 immediately before and/or during regular mealtimes of the subject, and/or withhold driving electrodes 28 at one or more designated times in a 24-hour cycle, e.g., times of day that are not regular mealtimes of the subject, and especially, times of day during which the subject is usually sleeping. Typically, sensor 44 provides feedback that indicates when the stimulation should stop. Thus, for example, control unit 30 may stop driving the electrodes in response to the blood-glucose sensor detecting that the blood-glucose level of subject 26 is normal or low.

In some applications, control unit 30 drives electrodes 28 to drive a sequence of bursts of electric current, the bursts being separated by respective time intervals, each of which having a duration of at least 2 minutes, less than 8 minutes, and/or between 2 and 8 minutes. As noted in Matveyenko et al. Pulsatile portal vein insulin delivery enhances hepatic insulin action and signaling, Diabetes, 2012, insulin is secreted as discrete insulin secretory bursts at approximately 5-minute intervals into the hepatic portal vein, these pulses being attenuated early in the development of type 1 and type 2 diabetes mellitus. Hence, by driving a sequence of bursts of electric current in the manner described above, the pancreas is typically stimulated to secrete insulin in a manner that is similar to the manner in which a healthy pancreas secretes insulin. The inventor hypothesizes that it may be beneficial to stimulate the pancreas of the subject to secrete insulin in the above-described "natural" manner. The above-described technique for driving electric current may be used in combination with any of the apparatus and methods described herein, such as with methods 62 and 64, described hereinbelow with reference to FIGS. 5-6.

In some applications, control unit 30 is configured to communicate with an external device, such as a smartphone or computer belonging to the subject and/or a physician. For example, the control unit may communicate the subject's blood glucose levels at various times. The control unit may also communicate the times at which the stimulation device was activated, and/or the duration of each activation.

Figure 3:
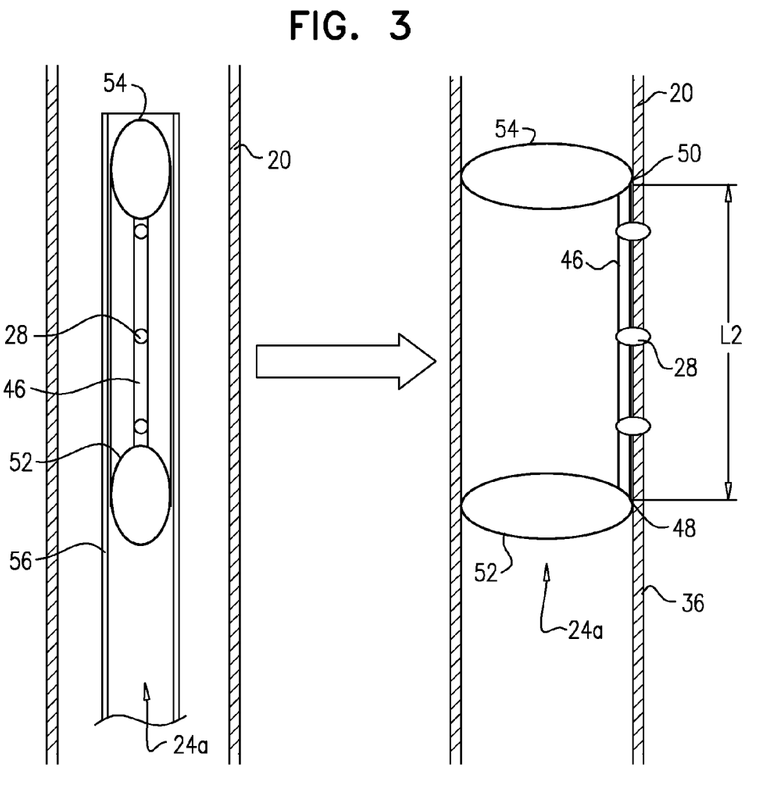
FIG. 3 is a schematic illustration of an intravascular support structure, in accordance with some applications of the present invention.

Reference is now made to FIG. 3, which is a schematic illustration of an intravascular support structure 24*a*, which is a particular implementation of intravascular support structure 24, in accordance with some applications of the present invention. In general, all of the features and techniques described above with reference to FIGS. 1-2 may be applied to and/or practiced with intravascular support structure 24*a*.

For example, at least a portion of intravascular support structure 24a and/or the electrodes coupled thereto may be radiopaque, sensor 44 may be used to provide input to control unit 30, etc.

In some applications, as shown in FIG. 3, intravascular support structure 24a comprises a longitudinal element 46 having a proximal end 48 and a distal end 50. A first stabilizing ring 52 is coupled to proximal end 48, and a second stabilizing ring 54 is coupled to distal end 50. At least one of electrodes 28 is coupled to longitudinal element 46 and/or to at least one of stabilizing rings 52 and 54. Longitudinal element 46 typically has a length L2 that is at least 3 cm, less than 10 cm, and/or between 3 and 10 cm. (L2 is typically approximately a typical width of a pancreas.)

As shown in FIG. 3, intravascular support structure 24a is typically placed in the blood vessel (e.g., inferior vena cava 20) via a catheter 56. While contained inside catheter 56, intravascular support structure 24a is in a constrained configuration, such that stabilizing rings 52 and 54 are substantially aligned with the longitudinal axis of longitudinal element 46. Upon intravascular support structure 24a reaching the desired placement site, catheter 56 is withdrawn, and intravascular support structure 24a adopts an unconstrained configuration, in which stabilizing rings 52 and 54 are substantially transverse to the longitudinal axis of longitudinal element 46, and are in contact with wall 36 of the blood vessel. By contacting wall 36, stabilizing rings 52 and 54 stabilize intravascular support structure 24a, and/or generally prevent intravascular support structure 24a from moving from the placement site.

Figure 4:
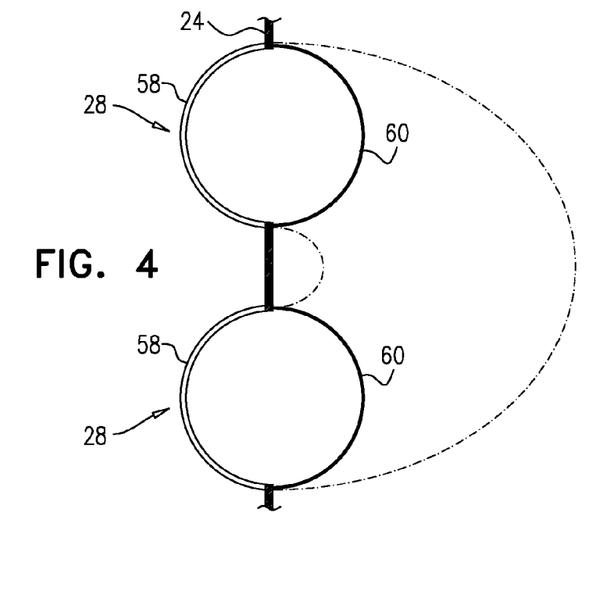
FIG. 4 is a schematic illustration of two cross-sections of electrodes, in accordance with some applications of the present invention.

Reference is now made to FIG. 4, which is a schematic illustration of two cross-sections of electrodes 28, in accordance with some applications of the present invention. Each of the cross-sections is shown having a perimeter consisting of a first contiguous portion 58, and a second contiguous portion 60. In some applications, for at least one of electrodes 28, the electrode is insulated along first contiguous portion 58, and is not insulated along second contiguous portion 60. Typically, first contiguous portion 58 includes at least 50% (e.g., at least 65%) of the perimeter. The insulation along portion 58 of the perimeter generally prevents current from being driven in the wrong direction, thus typically conserving power and/or preventing unwanted side effects in the subject. Insulated electrodes 28 may be used in combination with any of the apparatus or methods described herein. For example, insulated electrodes may be used to stimulate the pancreas at a plurality of locations along its length and width, as described above with reference to FIG. 2.

Figure 5:
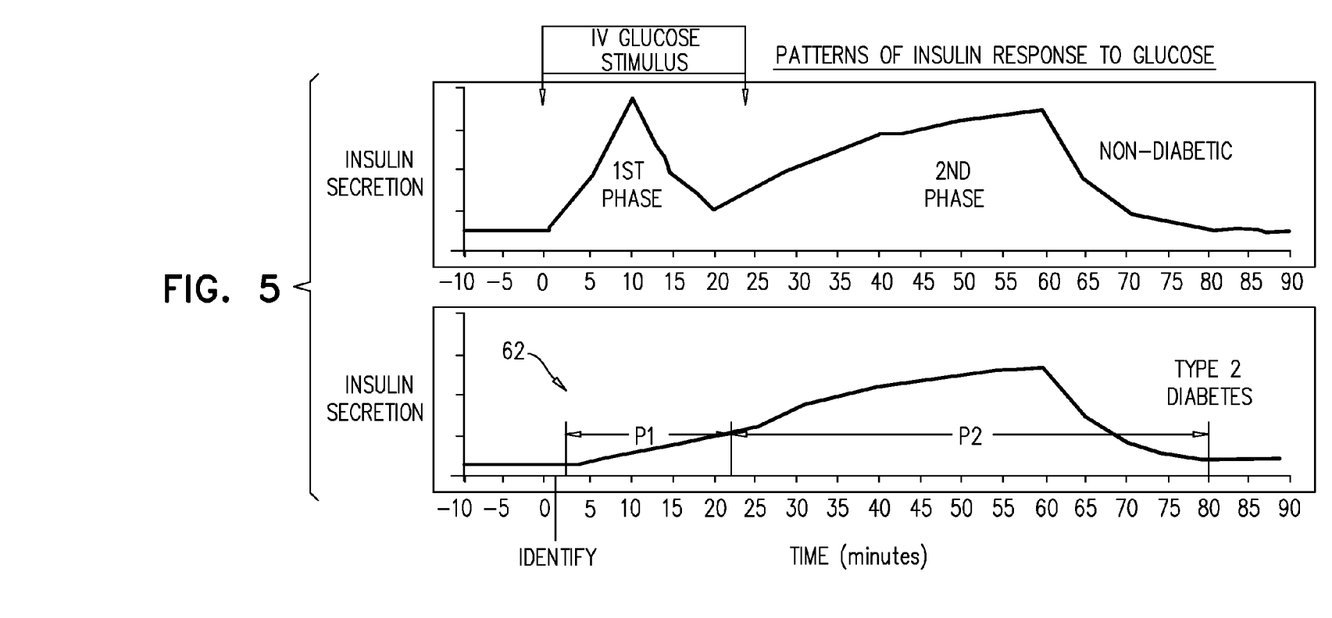
FIGS. 5 and 6 are schematic illustrations of respective methods of stimulating a pancreas of a subject, in accordance with some applications of the present invention.

Reference is now made to FIG. 5, which is a schematic illustration of a method 62 of stimulating a pancreas of a subject, in accordance with some applications of the present invention. FIG. 5 shows indicia relating to method 62 overlaid on a downloaded image, which shows respective patterns of insulin response to glucose for both a typical non-diabetic subject (top graph), and a typical diabetic subject (bottom graph). (Being that this image is being used for illustrative purposes only, the description of the image presented herein may deviate slightly from the description provided at the image source.)

During the period of time from 0 to 25 minutes, glucose was administered intravenously to the subjects. (The intravenous administration of glucose may be considered a proxy for a typical intake of glucose from a meal.) As shown in the top graph, the pancreas of the non-diabetic subject responded by secreting insulin in two phases, the first phase being relatively sharp and immediate, and the second phase being a more gradual, delayed response. As shown in the bottom graph, the response of the pancreas of the diabetic subject was lacking the first phase of insulin secretion, such that the pattern of the response was similar to the second-phase response of the non-diabetic subject.

In light of these observed patterns of insulin response, the inventor hypothesizes that it may be beneficial to stimulate the pancreas of subject 26 only during a period of time that roughly corresponds to the first phase of insulin secretion. Accordingly, in method 62, a plurality of electrodes (which may include electrodes 28) disposed within the subject's body are driven to stimulate pancreas 22 during a first period of time P1 that roughly corresponds to the first phase of insulin secretion, but not during a second period of time P2 that immediately follows P1. It is first identified (e.g., via an eating sensor and/or glucose sensor included in sensor 44 of FIG. 2) that subject 26 is eating. (Time 0 on the graph indicates the time at which the subject begins eating, with the identifying being shortly thereafter.) Period P1 begins less than 15 minutes (e.g., less than 10 minutes, and/or less than 5 minutes) after the identifying, and has a duration that is at least 10 minutes but is typically less than 30 minutes, e.g., less than 20 minutes. The duration of P2 is at least 30 minutes and/or at least 50 minutes, but is typically less than 90 minutes.

In some applications, the pancreas is continuously or periodically stimulated with a basal level of stimulation. Then, upon identifying that the subject is eating, the pancreas is stimulated during period of time P1 with a level of stimulation that is greater than the basal level of stimulation.

Figure 6:
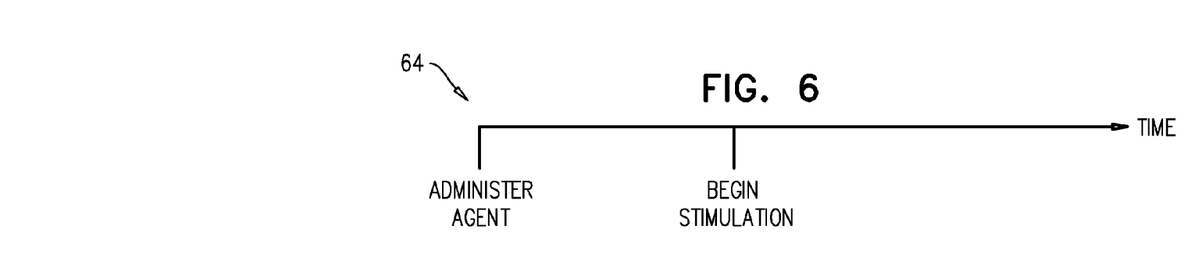

Reference is now made to FIG. 6, which is a schematic illustration of a method 64 of stimulating a pancreas of a subject, in accordance with some applications of the present invention. Method 64 comprises administering a glucagon-secretion-inhibiting agent (e.g., vildagliptin) and/or a glucagon antagonist (i.e., an antagonist of the blood-glucose-increasing effect of glucagon, e.g., metformin) to the subject. While the subject is affected by the administered agent, a plurality of electrodes disposed within the subject's body are driven to stimulate pancreas 22 by driving an electric current through tissue of the pancreas. For example, at least one electrode 28 (FIGS. 1-4) disposed within a blood vessel of the subject may be driven to stimulate pancreas 22.

The inventor hypothesizes that without the administration of the glucagon-secretion-inhibiting agent, it is possible that electric current that is driven through the pancreas will stimulate both the alpha cells and beta cells of the pancreas. Although it is desirable to stimulate the beta cells, it is typically not desirable to stimulate the alpha cells, since these cells secrete glucagon, which counteracts the effect of insulin by elevating glucose levels in the blood. Therefore, via the administration of the glucagon-secretion-inhibiting agent prior to stimulation of the pancreas, method 64 generally decreases the extent to which the alpha cells are stimulated. Alternatively or additionally, the administration of the glucagon antagonist generally decreases the extent to which the secreted glucagon elevates the level of glucose in the blood of the subject.

Method 62 or method 64 may be practiced in combination with apparatus and methods described above with reference to FIGS. 1-4, and/or may be practiced in combination with other electrodes disposed within the subject's body. Furthermore, methods 62 and 64 may be practiced in combination with one another.

Figure 8:
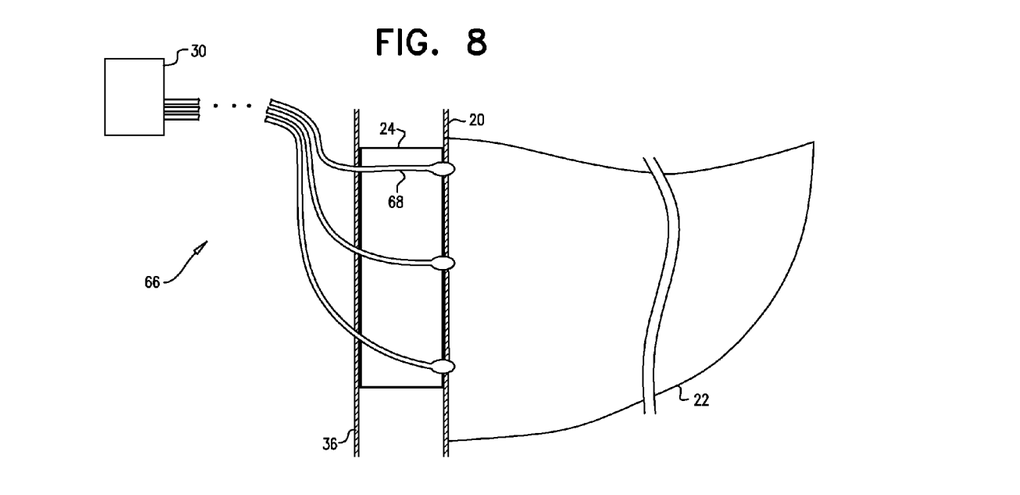
FIG. 8 is a schematic illustration of a method for stimulating a pancreas of a subject, in accordance with some applications of the present invention.

Reference is now made to FIG. 8, which is a schematic illustration of a method 66 for stimulating a pancreas of a subject, in accordance with some applications of the present invention. In some applications, the distal end of at least one lead 68 is placed within a blood vessel (e.g., the vena cava or aorta) of the subject, within 2 cm (e.g., within 1 cm, e.g., within 5 mm) of the pancreas. Control unit 30 is implanted in the subject, and is connected to the proximal end of lead 68, such that the control unit may stimulate the pancreas via the lead. Method 66 is generally similar to methods for stimulation described hereinabove with reference to FIGS. 1-4, in that the distal end of the lead is effectively an electrode. In general, method 66 may be practiced in combination with any of the apparatus or techniques described hereinabove, with reference to any of the figures.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
    identifying that it is desired to apply electrical stimulation to a pancreas of a subject;
    in response to the identifying, placing an intravascular support structure within an inferior vena cava of the subject, the intravascular support structure having at least one electrode coupled thereto, the at least one electrode being configured to stimulate the pancreas of the subject by driving an electric current through tissue of the pancreas of the subject;
    using a control unit to drive the at least one electrode to drive the electric current by sending a signal to the electrode; and
    identifying that the subject is eating,
    wherein using the control unit to drive the at least one electrode to drive the electric current comprises:
    in response to the identifying, during a first period of time beginning less than 15 minutes after the identifying and having a duration of at least 10 minutes, driving the at least one electrode to drive the electric current; and
    during a second period of time that immediately follows the first period of time and has a duration of at least 30 minutes, withholding driving the at least one electrode to drive the electric current.

2. The method according to claim 1, wherein placing the intravascular support structure within the inferior vena cava comprises penetrating a wall of the inferior vena cava with the at least one electrode that is coupled to the intravascular support structure.

3. The method according to claim 1, wherein placing the intravascular support structure within the inferior vena cava comprises placing the intravascular support structure between a superior mesenteric vein and a portal vein.

4. The method according to claim 1,
    wherein at least a portion of an element selected from the group consisting of: the intravascular support structure, and the at least one electrode, is radiopaque,
    wherein the method further comprises viewing a fluoroscopic image of the radiopaque portion, when the radiopaque portion is inside the inferior vena cava, and
    wherein placing the intravascular support structure within the inferior vena cava of the subject comprises aligning the at least one electrode with respect to the pancreas, in response to the viewing.

5. The method according to claim 1, wherein using the control unit to drive the at least one electrode to drive the electric current comprises using the control unit to drive the at least one electrode from outside a body of the subject.

6. The method according to claim 1, wherein driving the at least one electrode to drive the electric current during the first period of time comprises driving the at least one electrode to drive the electric current during a period of time that begins less than 10 minutes after the identifying.

7. The method according to claim 1, wherein using the control unit to drive the at least one electrode to drive the electric current comprises using the control unit to drive the at least one electrode to drive a current having a frequency between 2 and 20 Hz.

8. The method according to claim 1, wherein using the control unit to drive the at least one electrode to drive the electric current comprises using the control unit to drive the at least one electrode to drive a current having an amplitude between 1 and 8 mA.

9. The method according to claim 1,
    wherein the at least one electrode includes at least a first electrode, a second electrode, and a third electrode, and
    wherein using the control unit to drive the at least one electrode to drive the electric current comprises using the control unit to:
    drive the first electrode and the second electrode to drive a first electric current therebetween,
    drive the first electrode and the third electrode to drive a second electric current therebetween, and
    drive the second electrode and the third electrode to drive a third electric current therebetween.

10. The method according to claim 1, further comprising using a sensor to detect a physiological parameter of the subject, wherein using the control unit to drive the at least one electrode to drive the electric current comprises using the control unit to drive the at least one electrode to drive the electric current in response to the detected physiological parameter.

11. The method according to claim 10, wherein using the sensor to detect the physiological parameter of the subject comprises using the sensor to detect a blood-glucose level of the subject, and wherein using the control unit to drive the at least one electrode to drive the electric current comprises using the control unit to drive the at least one electrode to drive the electric current in response to the blood-glucose level of the subject.

12. The method according to claim 10, wherein using the sensor to detect the physiological parameter of the subject comprises using the sensor to detect a heart rate of the subject, and wherein using the control unit to drive the at least one electrode to drive the electric current comprises using the control unit to drive the at least one electrode to drive the electric current in response to the heart rate of the subject.

13. The method according to claim 1, wherein using the control unit to drive the at least one electrode to drive the electric current comprises using the control unit to drive the at least one electrode to drive the electric current in response to a time of day.

14. A method comprising:
    identifying that it is desired to apply electrical stimulation to a pancreas of a subject; and
    in response to the identifying, placing an intravascular support structure within an inferior vena cava of the subject, the intravascular support structure having at least one electrode coupled thereto, the at least one electrode being configured to stimulate the pancreas of the subject by driving an electric current through tissue of the pancreas of the subject, wherein placing the intravascular support structure within the inferior vena cava comprises penetrating a wall of the inferior vena cava with the at least one electrode that is coupled to the intravascular support structure, and wherein penetrating the wall of the inferior vena cava comprises penetrating completely through the wall of the inferior vena cava.

15. The method according to claim 14, further comprising using a control unit to drive the at least one electrode to drive the electric current by sending a signal to the electrode.

16. A method comprising:
identifying that it is desired to apply electrical stimulation to a pancreas of a subject;
in response to the identifying, placing an intravascular support structure within an inferior vena cava of the subject, the intravascular support structure having at least one electrode coupled thereto, the at least one electrode being configured to stimulate the pancreas of the subject by driving an electric current through tissue of the pancreas of the subject;
using a control unit to drive the at least one electrode to drive the electric current by sending a signal to the electrode; and
using a sensor to detect that the subject is eating, wherein using the control unit to drive the at least one electrode to drive the electric current comprises using the control unit to drive the at least one electrode to drive the electric current in response to detecting that the subject is eating.

17. A method comprising:
identifying that it is desired to apply electrical stimulation to a pancreas of a subject;
in response to the identifying, placing an intravascular support structure within an inferior vena cava of the subject, the intravascular support structure having at least one electrode coupled thereto, the at least one electrode being configured to stimulate the pancreas of the subject by driving an electric current through tissue of the pancreas of the subject; and
using a control unit to drive the at least one electrode to drive the electric current by sending a signal to the electrode,
wherein using the control unit to drive the at least one electrode comprises withholding driving the at least one electrode at one or more designated times in a 24-hour cycle.

18. The method according to claim 17, wherein the method further comprises identifying that the subject is eating, and wherein using the control unit to drive the at least one electrode to drive the electric current comprises:
in response to the identifying, during a first period of time beginning less than 15 minutes after the identifying and having a duration of at least 10 minutes, driving the at least one electrode to drive the electric current; and
during a second period of time that immediately follows the first period of time and has a duration of at least 30 minutes, withholding driving the at least one electrode to drive the electric current.

* * * * *